March 7, 1967 W. FLEMER, JR Plant Pat. 2,726
GINKGO TREE
Filed Sept. 28, 1965
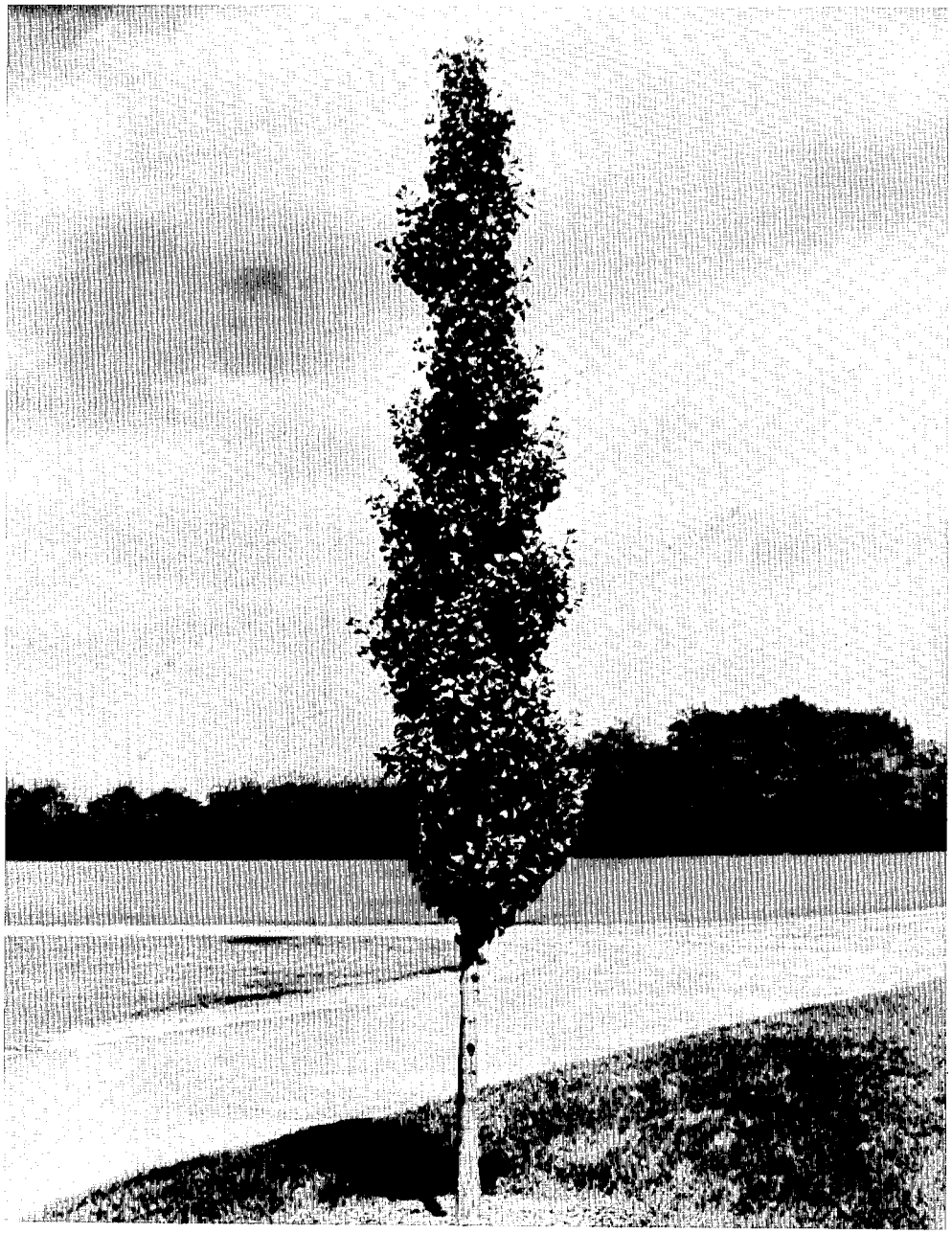
Inventor.
William Flemer, Jr.
By: Robb & Robb
Attorneys.

United States Patent Office

Plant Pat. 2,726
Patented Mar. 7, 1967

2,726
GINKGO TREE

William Flemer, Jr., Princeton, N.J., assignor, by mesne assignments, to Treesearch, Kingston, N.J., a partnership Filed Sept. 28, 1965, Ser. No. 491,050
1 Claim. (Cl. Plt.—51)

The present invention relates to a new and distinct variety of Ginkgo tree which was originated by me as an open-pollinated seedling of an unpatented female clone of *Ginkgo biloba fastigiata* grown by me in South Brunswick Township, New Jersey.

As the result of this breeding, I have produced a new and improved variety of Ginkgo tree which is distinguished from its parent, as well as from all other varieties of which I am aware, as evidenced by the following unique combination of characteristics which are outstanding therein:

(1) A naturally narrow and perfectly symmetrical tree crown composed of short and evenly spaced fastigiate branches, without the need of special or corrective pruning;

(2) A strong central leader or trunk which grows naturally straight and vertical without the corrective staking usually necessary for other grafted Ginkgo clones;

(3) Ease of propagation either by means of grafting onto seedling understocks or by soft wood cuttings;

(4) Good resistance to marginal leaf scorch exhibited by other Ginkgo trees of seedling origin grown under identical conditions in South Brunswick Township, New Jersey; and (5) Complete freedom from the production of ill-smelling fruit as usually borne by female Ginkgo trees, as a consequence of its male sex.

A sexual reproduction of my new variety by both grafting and vegetative cuttings, as performed in South Brunswick Township, New Jersey, shows that the foregoing characteristics and distinctions come true and are established and transmitted through succeeding propagations.

The accompanying drawing shows a typical specimen tree of my new variety of Ginkgo tree which illustrates its characteristic habits of growth.

The following is a detailed description of my new variety, with color terminology in accordance with the Nickerson Color Fan, published by Munsell Color Company, Inc., of Baltimore, Maryland, except where general color terms of ordinary dictionary significance are obvious, as based on specimens grown in South Brunswick Township, New Jersey:

Parentage: An open-pollinated seedling of a female clone of *Ginkgo biloba fastigiata.*

Propagation: Holds its distinguishing characteristics through succeeding propagations by both grafting and cuttings.

Tree: Medium size; tall (about 26 feet at age of about 20 years); 4 feet wide; fastigiate; extremely narrow head; hardy.

*Trunk.*—Stocky; rough.

*Branches.*—Curved upwards; short; stocky; rough when mature.

*Head or crown.*—Regular; very narrow; branches evenly spaced around a central leader; excurrent branching habit.

*Lenticels.*—Few; large.

Foliage:

*Leaves.*—Abundant; thick; leathery. Length (including petiole)—from about 11 cm. to 13 cm. Width—from about 10 cm. to 11 cm. Shape—fan-shaped; shallowly incised into 2 lobes, with depth of sinus approximately ⅓ depth of blade, with sinus from about 1½ cm. to 2 cm. deep. Color—Moderate Olive Green, Plate 7.5GY 4/4. Margin—sinuate. Petiole—long (from about 5 cm. to 7 cm. long). Glands—none. Stipules—none.

Flower buds: Hardy; hemispherical. Color—brown.

Flowers: Long staminate catkin; not ornamental.

*Size.*—Normal.

*Length.*—From about 3.5 cm. to 3.7 cm. long.

*Width.*—About 1 cm.

*Quantity.*—Few.

Fruit: None; entirely free from the production of ill-smelling fruit usually borne by female Ginkgo trees, due to male sex.

I claim:

A new and distinct variety of Ginkgo tree, substantially as herein shown and described, characterized particularly as to novelty by the unique combination of a naturally narrow and perfectly symmetrical tree crown composed of short and evenly spaced fastigiate branches, a strong central leader or trunk which grows naturally straight and vertical, ease of propagation by both grafting and cuttings, good resistance to marginal leaf scorch, and complete freedom from the production of ill-smelling fruit.

References Cited by the Examiner

Trees for American Gardens, Wyman, 1951, pp. 184–186 relied on.

Scanlon Tailored Trees, 1962–1963 catalog, p. 39 relied on.

ABRAHAM G. STONE, *Primary Examiner.*

ROBERT E. BAGWILL, *Examiner.*